US005434615A

United States Patent [19]
Matumoto

[11] Patent Number: 5,434,615
[45] Date of Patent: Jul. 18, 1995

[54] SIGNAL PROCESSING CIRCUIT ADAPTABLE TO ELECTRONIC ENDOSCOPES HAVING DIFFERENT LENGTHS

[75] Inventor: Seizi Matumoto, Omiya, Japan

[73] Assignee: Fuji Photo Optical Co., Ltd., Omiya, Japan

[21] Appl. No.: 119,592

[22] Filed: Sep. 13, 1993

[30] Foreign Application Priority Data

Sep. 25, 1992 [JP] Japan .................. 4-280791

[51] Int. Cl.⁶ .................................. A61B 1/04
[52] U.S. Cl. ........................... 348/72; 348/518
[58] Field of Search ............ 348/72, 518; H04N 7/18

[56] References Cited

U.S. PATENT DOCUMENTS 4,807,025  2/1989  Eino ........................... 348/72
4,845,555  7/1989  Yabe .......................... 348/72

FOREIGN PATENT DOCUMENTS

62-253275  5/1987  Japan .

Primary Examiner—Howard W. Britton
Attorney, Agent, or Firm—Oliff & Berridge

[57] ABSTRACT

A signal processor apparatus is adaptable to electronic endoscopes having different lengths without the need for changing the operation timing when sampling a video signal. A sampling pulse generator incorporating a phase varying means is disposed in the operating portion or the connecting portion (setup board) of an electronic endoscope. A sampling pulse having the timing corresponding to the length of the electronic endoscope is formed by varying the phase of the sampling pulse by the phase varying means. The sampling pulse generator may be disposed together with a sample-and-hold circuit, a driving circuit of a CCD and the like. Since it is possible to sample and hold the video signal by using the sampling pulse which is correspondent with the length of the electronic endoscope, effective picture signal processing by the processor apparatus is enabled.

8 Claims, 7 Drawing Sheets

PRIOR ART

F I G. 13

SIGNAL PROCESSING CIRCUIT ADAPTABLE TO ELECTRONIC ENDOSCOPES HAVING DIFFERENT LENGTHS

BACKGROUND OF THE INVENTION

This application claims the priority of Japanese Patent Application No. 4-280791 filed on Sep. 25, 1992 which is incorporated herein by reference.

1. Field of the Invention

The present invention relates to a signal processing circuit for an electronic endoscope which processes a video signal obtained by a solid-state image sensor so as to display an image.

2. Description of the Related Art

Electronic endoscopes used in medical and industrial fields are known. Such an electronic endoscope is inserted into a body cavity such as an alimentary canal and a structural body through an electronic endoscope provided with a CCD (Charge Coupled Device) as a solid-state image sensor at the end portion thereof so as to observe the body cavity.

Figure 13:
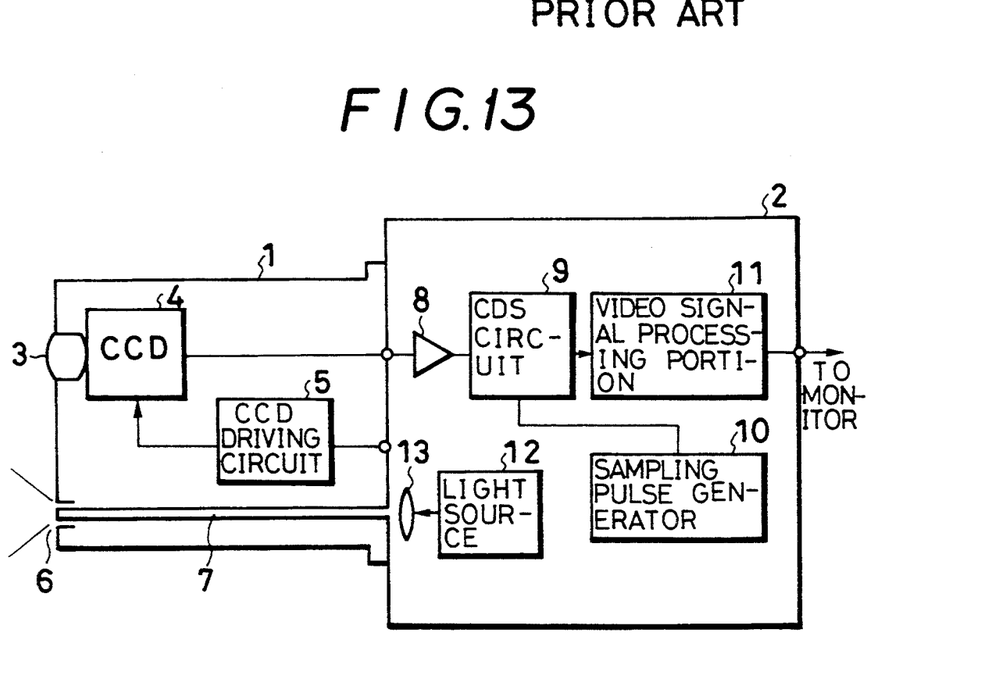
FIG. 13 shows the structure of a conventional signal processing circuit for an electronic endoscope.

FIG. 13 shows the structure of a conventional electronic endoscope. An electronic endoscope 1 is removably connected to a processor apparatus 2 through a connector. In the end portion of the electronic endoscope 1 are provided a CCD 4 which is optically connected to an observation window 3, a CCD driving circuit 5, a light projection window 6 for projecting observation light therethrough into a body cavity and a light guide (optical fiber) 7 for providing light to the light projection window 6. In the processor apparatus 2, a correlated double sampling (CDS) circuit 9 is provided so as to be connected to the CCD 4 through an amplifier 8. A sampling pulse generator 10 provides a sampling pulse for the CDS circuit 9. A video signal processing portion 11 for executing gamma correction, white balancing, etc. and having a memory or the like is connected to the CDS circuit 9. The processor apparatus 2 is further provided with a light source device 12 and a condenser lens 13. The light source device 12 provides predetermined light (RGB beams in a surface sequential processing system) for the light guide 7 in the electronic endoscope 1.

According to the above-described structure, the light output from the light source device 12 is projected into a body cavity through the light projection window 6 of the electronic endoscope 1, so that the image of the object of observation is taken by the CCD 4 which is driven by the CCD driving circuit 5. A video signal output from the CCD 4 is supplied to the CDS circuit 9 through the amplifier 8. The CDS circuit 9 subjects the output of the CCD 4 to clamping processing, and samples and holds the video signal portion which contains image information. In this case, the sampling processing is executed on the basis of the output of the sampling pulse generator 10, and the video signal portion is sampled and held by a sampling pulse whose phase is adjusted in relation to the clamping pulse. Due to the correlated double sampling, the noise in the video signal is favorably reduced.

After the gamma correction processing of the output of the CDS circuit 9 by the video signal processing portion 11, the signal is output to a monitor which is connected to the processor apparatus 2. In this manner, the monitor displays the color image of the body cavity as the object of observation.

However, when the conventional signal processing circuit for an electronic endoscope is used for electronic endoscopes 1 having different lengths, the timing of clamping, sampling, and holding the video signal output from the CCD 4 varies in accordance with the length, so that it is impossible to effectively operate the CDS circuit 9. There are electronic endoscopes 1 having different lengths in correspondence with the objects of observation. If electronic endoscopes 1 having different lengths are connected to the processor apparatus 2, it is necessary to provide the sampling pulse and the like for the CDS circuit 9 with an operation timing which is determined in consideration of the time for transmitting the video signal through the length of the corresponding electronic endoscopes 1. In this case, the processor apparatus 2 may be provided with a circuit or the like for changing the operation timing depending on the length of the electronic endoscope 1. Then the structure of the circuit becomes complicated, and it is laborious to exchange the electronic endoscopes 1.

In order to solve this problem, a sample-and-hold circuit is conventionally provided at the end portion of the electronic endoscope 1 on the same chip as the CCD 4 or independently thereof, as disclosed in Japanese Patent Publication No. 75118/1991. In this case, however, the outer diameter of the end portion becomes large, which is an obstacle to the reduction in the diameter of the electronic endoscope. In addition, when the sample-and-hold circuit is provided at the end portion, the consumption of electric power at the end portion becomes large, which results in the rise in the temperature of the end portion which is to be inserted into a body cavity and an increase in the nonuniformity of dark current which is generated on the surface of the silicon substrate of the CCD 4, thereby deteriorating the performance of the CCD 4.

SUMMARY OF THE INVENTION

Accordingly, it is an object of the present invention to eliminate the above-described problems in the related art and to provide a signal processing circuit for an electronic endoscope which is capable of effectively operating a correlated double sampling circuit or the like without changing the operation timing when it is used for electronic endoscopes having different lengths, and which has a simplified structure and is easy to handle.

To achieve this aim, a signal processing circuit for an electronic endoscope according to the present invention comprises: a sampling pulse generator which is disposed in the operating portion or the connecting portion (setup board) of the electronic endoscope, and a phase varying means incorporated into the sampling pulse generator so as to vary the pulse phase and output a sampling pulse with the timing corresponding to the length of the electronic endoscope. It is preferable that the signal processing circuit further comprises a sample-and-hold circuit for sampling and holding a video signal by using the sampling pulse disposed within the electronic endoscope except at the end portion thereof.

According to this structure, since it is possible to dispose the sampling pulse generator which incorporates the phase varying means in the electronic endoscope independently of or together with the sampling circuit, the sampling pulse having the timing corresponding to the length of the electronic endoscope is set for each electronic endoscope. Therefore, when electronic endoscopes having different lengths are connected to the processor apparatus, it is not necessary to take the operation of sample-and-hold circuit into consideration.

As the sample-and-hold circuit, a correlated double sampling circuit utilizing a clamping pulse and a sampling pulse which are correlated with each other may be provided, and the sampling pulse generator adjusts the phases of the clamping pulse and the sampling pulse by the phase varying means. A differential delay noise eliminating circuit may be provided as the sample-and-hold circuit.

As the phase varying circuit of the sampling pulse generator, a combinational circuit of a variable resistor and a capacitor may be used, thereby forming a clamping pulse having a timing corresponding to the length of the electronic endoscope. At the next stage to the combinational circuit of a variable resistor and a capacitor may be provided a combinational circuit of a resistor and a capacitor, thereby forming a sampling pulse whose phase is shifted by a predetermined amount from the clamping pulse. With the clamping pulse and the sampling pulse obtained from the sampling pulse generator which are correlated with each other, it is possible to subject the video signal output from the solid-state image sensor in the electronic endoscope to a correlated double sampling processing.

In addition, a driving circuit for driving the solid-state image sensor may be disposed in the operating portion or the connecting portion of the electronic endoscope together with the sampling pulse generator which incorporates the phase varying means. In this case, it is possible to simplify the circuit structure and ward off the influence of the heat of the driving circuit and the electric source which is inevitable when they are disposed at the end portion of the electronic endoscope, thereby securing the reliable video signal processing operation.

The above and other objects, features and advantages of the present invention will become clear from the following description of the preferred embodiments thereof, taken in conjunction with the accompanying drawings.

DESCRIPTION OF THE PREFERRED EMBODIMENTS

First Embodiment

Figure 1:
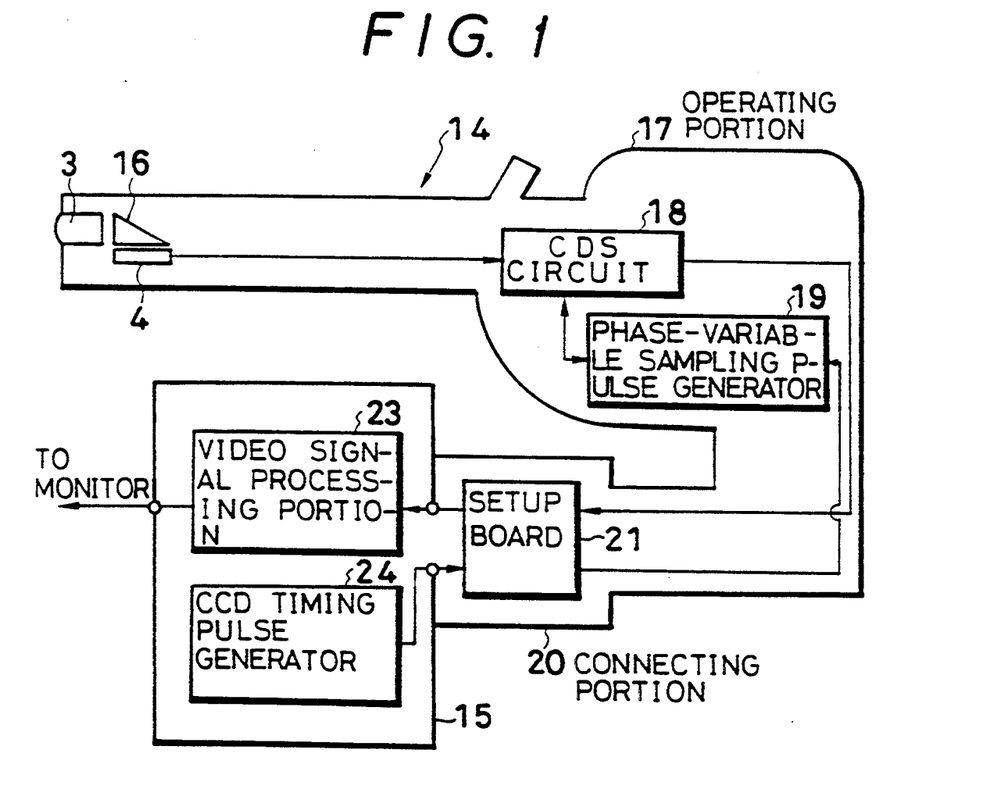
FIG. 1 shows the structure of a first embodiment of a signal processing circuit for an electronic endoscope according to the present invention.

FIG. 1 shows the structure of a first embodiment of a signal processing circuit for an electronic endoscope according to the present invention. In FIG. 1, an electronic endoscope 14 is connected to a processor apparatus 15. A CCD 4 is connected to an observation window 3 at the end portion of the electronic endoscope 14 through an optical member 16. The center portion of the electronic endoscope 14 is provided with an operating portion 17, and the operating portion 17 is provided with control switches (not shown) such as an angling knob for bending the end portion of the electronic endoscope 14 in the vertical or horizontal direction, a shutter, a freezing button and a hard copying button. In the first embodiment, the operating portion 17 is provided with a CDS circuit 18 as a sample-and-hold circuit and a phase-variable sampling pulse generator 19 for forming a clamping pulse and a sampling pulse and varying the phases thereof. The phase-variable sampling pulse generator 19 forms a clamping pulse and a sampling pulse having a timing corresponding to the length of the electronic endoscope.

In a connecting portion 20 of the electronic endoscope 14 is provided a setup board 21 for setting or adjusting conditions which are necessary for a video signal processing. In the processor apparatus 15 which is connected to the operating portion 17 through the setup board 21 is provided a video signal processing portion 23, a CCD timing pulse generator 24 and the like.

Figure 2:
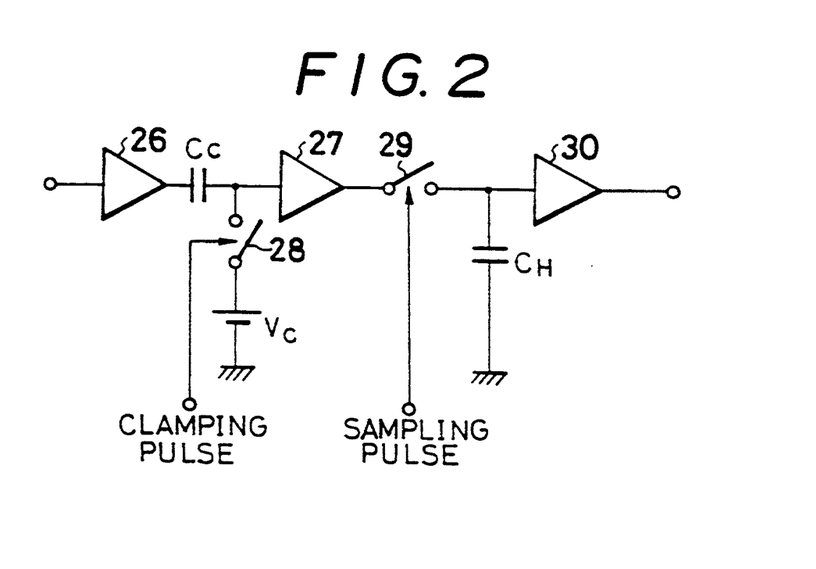
FIG. 2 is a circuit diagram of a CDS circuit of the first embodiment.

FIG. 2 shows the structure of the CDS circuit 18. In the CDS circuit 18, an amplifier 26, a capacitor Cc and an amplifier 27 are connected in series, and a reference power source Vc is connected between the capacitor Cc and the amplifier 27 through a switching circuit 28. A clamping pulse output from the phase-variable sampling pulse generator 19 shown in FIG. 1 is supplied to the switching circuit 28. An amplifier 30 is connected to the amplifier 27 through a gate circuit 29, and a capacitor CH is connected between the gate circuit 29 and the amplifier 30. A sampling pulse output from the phase-variable sampling pulse generator 19 is supplied to the gate circuit 29. The sampling pulse is a timing pulse which is correlated with the clamping pulse, and a correlated double sampling processing is executed by using these pulses. Since the phase-variable sampling pulse generator can adjust the phases of the clamping pulse and the sampling pulse, it is possible to form favorable clamping pulse and sampling pulse which correspond to the length of the electronic endoscope.

Figure 3:
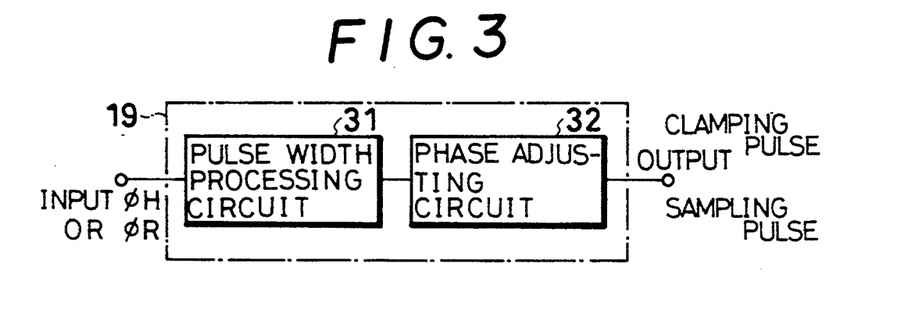
FIG. 3 is a block diagram of the structure of a phase-variable sampling pulse generator of the first embodiment.

FIG. 3 is a circuit diagram of the phase-variable sampling pulse generator 19 which is composed of a pulse width processing circuit 31 for adjusting the pulse width to a predetermined width and a phase adjusting circuit 32 as the phase varying means. A horizontal drive pulse φH or a reset pulse φR is provided for the pulse width processing circuit 31 and they are utilized to form a clamping pulse and a sampling pulse.

Figure 4:
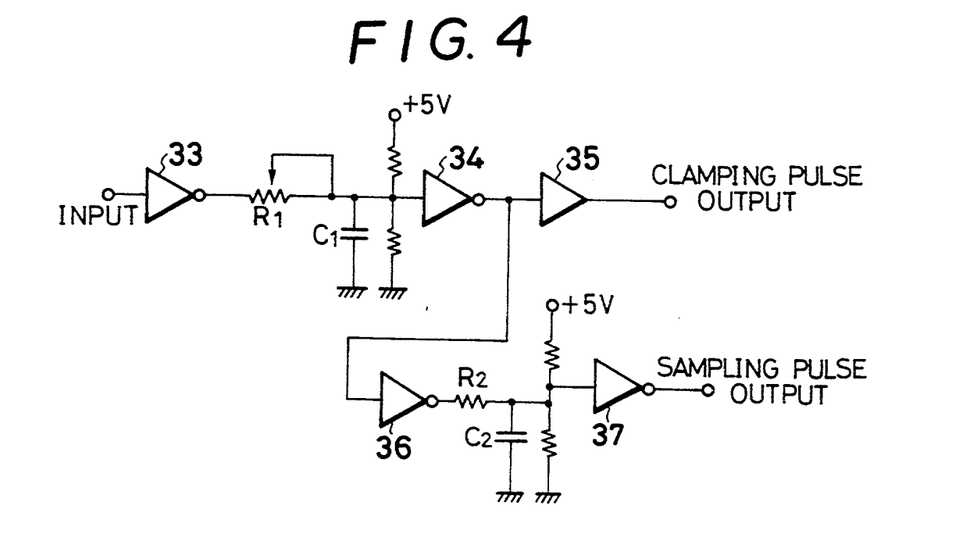
FIG. 4 is a circuit diagram of an example of a phase adjusting circuit as the phase varying means.
Figure 6:
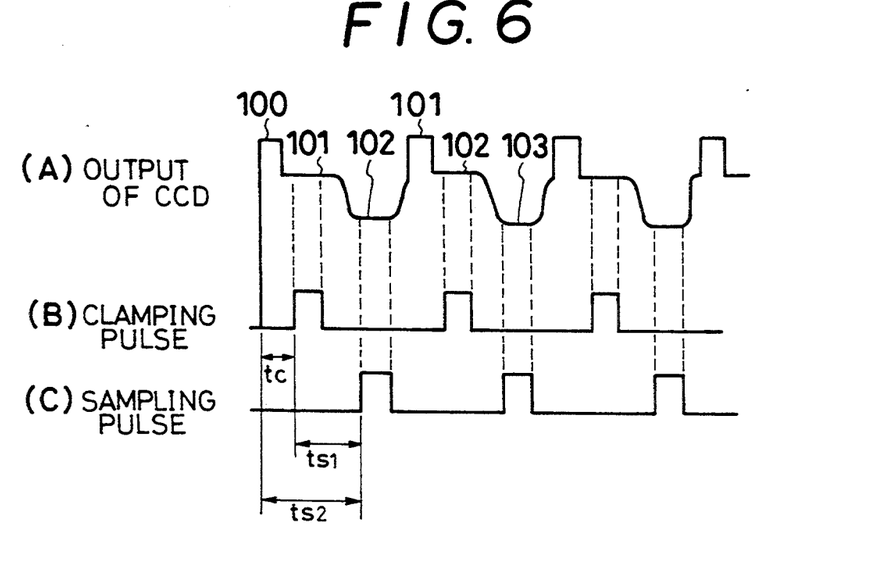
FIG. 6 shows the waveform of the operation of the first embodiment.

FIG. 4 shows the structure of the phase adjusting circuit 32. The phase adjusting circuit 32 is provided with inverters 33, 34, and a pulse amplifying element 35, and at the subsequent stage to the inverter 33 is provided an RC circuit composed of a variable resistor R1 and a capacitor C1, which functions as a delay circuit. When the reset pulse φR (100) is input to an input terminal, the input pulse is moved for a predetermined time tc by the RC circuit and used as a clamping pulse, as shown in FIG. 6. Since the predetermined time tc varies depending on the resistance of the variable resistor R1, it is possible to adjust the phase by varying the resistance of the variable resistor R1.

On the outputting side of the inverter 34, an RC circuit composed of a resistor R2 and a capacitor C2 is provided between inverters 36 and 37, and the output pulse of the inverter 34 shifts for a predetermined time ts1 (fixed time) which is determined by the RC circuit. The output pulse of the inverter 37 in this case is an input pulse to the input terminal which has shifted by the time tc+ts1. In this embodiment, this output of the inverter 37 is used as a sampling pulse. As described above, in this example, it is possible to adjust the phases of the clamping pulse and the sampling pulse in correspondence with the length of the electronic endoscope by using one variable resistor R1.

Figure 5:
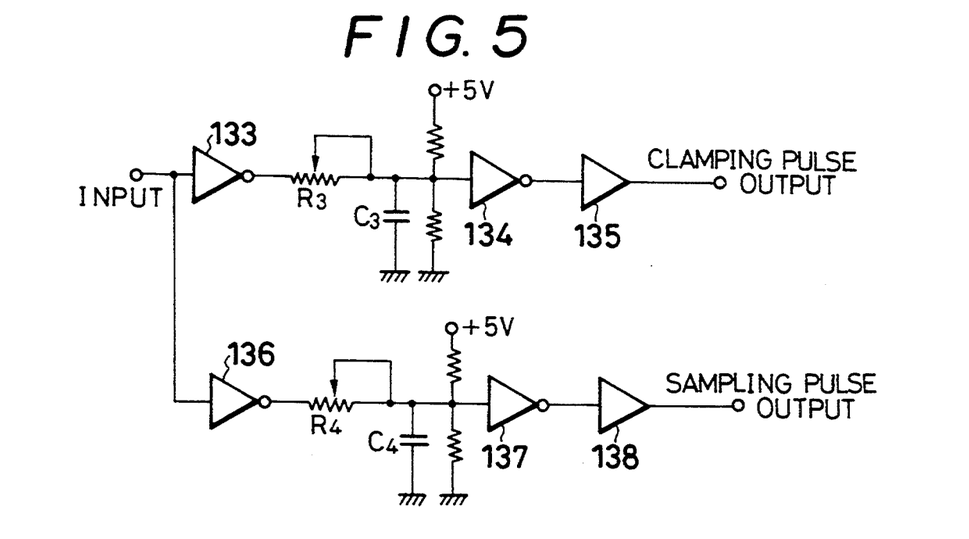
FIG. 5 is a circuit diagram of another example of the phase adjusting circuit.

FIG. 5 shows another example of the structure of the phase adjusting circuit 32. This structure enables the adjustment of the phases of the clamping pulse and the sampling pulse independently of each other. An Rc circuit composed of a variable resistor R3 and a capacitor C3 and an RC circuit composed of a variable resistor R4 and a capacitor C4 are provided between inverters 133 and 134 and between inverters 136 and 137, respectively. In this way, it is possible to form a clamping pulse by shifting, for example, a reset pulse φR (100) for a predetermined time tc and to form a sampling pulse by shifting the reset pulse φR for a predetermined time ts2, as shown in FIG. 6.

The operation of the first embodiment having the above-described circuit structure will be explained hereinunder with reference to FIG. 6. An image of an object of observation is taken by the CCD 4 through the observation window 3 shown in FIG. 1. The output of the CCD 4 is input directly to the CDS circuit 18. The output of the CCD 4 is composed of a reset pulse 100, a feedthrough portion (black level) 101, and a video signal portion 102 containing video information, as shown in FIG. 6(A). A clamping pulse shown in FIG. 6(B) and a sampling pulse shown in FIG. 6(C) are formed in the phase-variable sampling pulse generator 19 and input to the CDS circuit 18. When the clamping pulse is supplied to the switching circuit 28 shown in FIG. 2, the direct current of the feedthrough portion 101 is reproduced by the reference power source Vc. The predetermined time ts1 after the reproduction of the direct current, a sampling pulse is supplied to the gate circuit 29, thereby sampling and holding the video signal portion 102.

Since the sampling pulse is correlated with the clamping pulse, the output video signal of the CCD 4 is subjected to a correlated double sampling processing, so that a video signal whose noise is effectively eliminated is obtained. In this way, in the first embodiment, the operating portion 17 is provided with the CDS circuit 18 and the phase-variable sampling pulse generator 19, and the video signal is sampled by the clamping pulse and the sampling pulse which correspond to the length of the electronic endoscope 14. It is therefore not necessary to switch the sampling operation depending on the length of each electronic endoscope.

Figure 7:
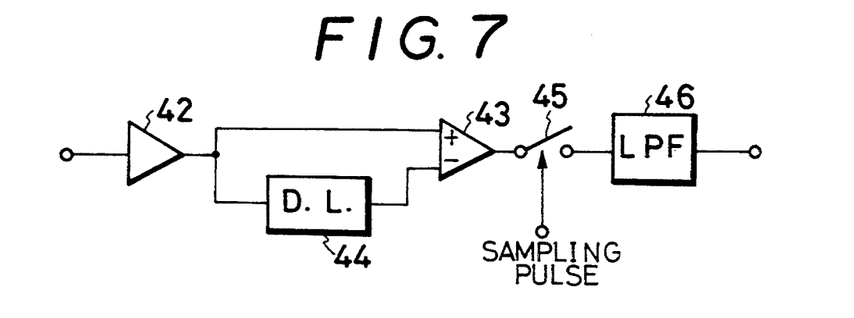
FIG. 7 is a circuit diagram of a differential delay noise eliminating circuit as another example of the sample-and-hold circuit in the first embodiment.
Figure 8:
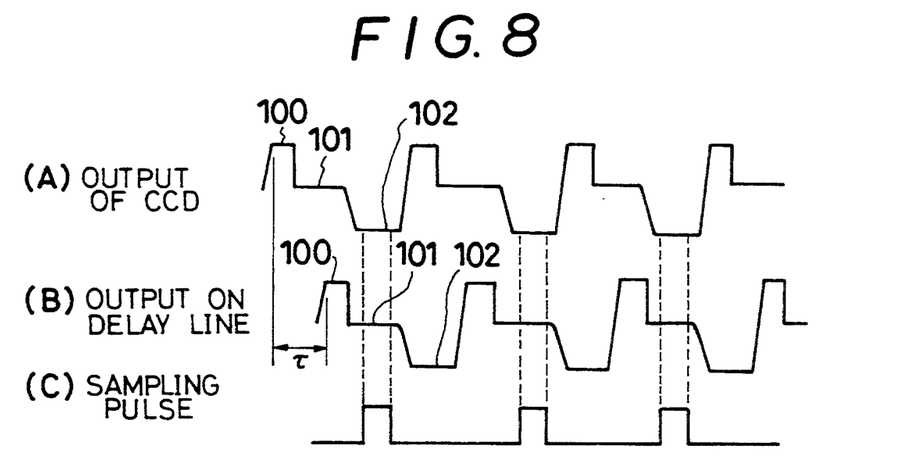
FIG. 8 shows the waveform of the operation of the differential delay noise eliminating circuit shown in FIG. 7.

FIG. 7 shows an example in which a differential delay noise eliminating circuit, which is similar to the correlated double sampling circuit, is used as the sample-and-hold circuit. In FIG. 7, one output of an amplifier 42 is connected to the positive terminal of an operation amplifier 43, and the other output is connected to the negative terminal of the operation amplifier 43 through a delay line 44. The operation amplifier 43 eliminates a noise component by subtracting the signal which is delayed by the time τ on the delay line 44 from the output signal of the CCD 4, as shown in FIG. 8. A gate circuit 45 is connected to the operation amplifier 43, and a low-pass filter (LPF) 46 is connected to the gate circuit 45. A sampling pulse whose phase is adjusted by the phase-variable sampling pulse generator 19 is supplied to the gate circuit 45.

According to this example, the output on the delay line shown in FIG. 8(B) is subtracted from the output of the CCD shown in FIG. 8(A). That is, the feedthrough portion 101 as the reference level is subtracted from the video signal portion 102, so that the noise included in the video signal is eliminated in such a manner as to eliminate the noise which exists in the feedthrough portion 101. Since the video signal portion 102 is sampled and held in the gate circuit 45 on the basis of the sampling pulse, it is possible to extract an excellent video signal by the differential delay noise eliminating circuit in the same way as by the correlated double sampling circuit.

Figure 9:
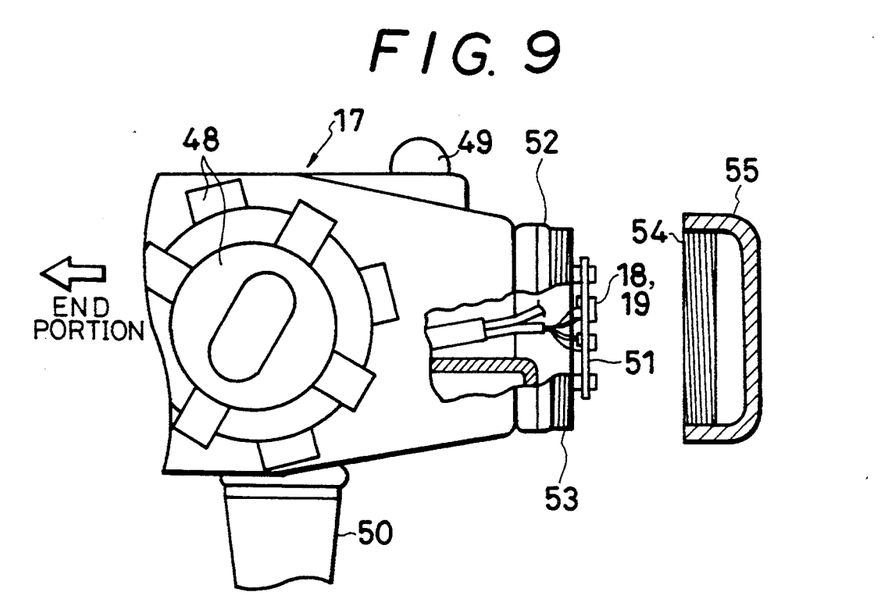
FIG. 9 shows the arrangement for attaching a circuit board to the operating portion in the first embodiment.

The arrangement for attaching the sample-and-hold circuit to the operating portion in the embodiment will now be explained with reference to FIG. 9. The operating portion 17 is of a convenient size for handling with one hand. It is provided with an angling knob (rotor) 48 for bending the end portion of the electronic endoscope 14, and a shutter 49, and is connected to the processor apparatus 15 through a cable 50. A circuit board housing 52 to which a circuit board 51 is attached is provided at the top portion of the operating portion 17, and the CDS circuit 18 and the phase-variable sampling pulse generator 19 are mounted on the circuit board 51.

The circuit board housing 52 has a male screw portion 53, and a cap 55 having a female screw portion 54 which engages with the male screw portion 53 is removably attached thereto. When the cap 55 is removed, it is easy to adjust phases by the phase-variable sampling pulse generator 19 mounted on the circuit board 51. That is, the adjustment of the phase of the sampling pulse which is inevitable at the time of manufacturing an electronic endoscope is facilitated by virtue of the cap 55 which is removably provided.

Second Embodiment

Figure 10:
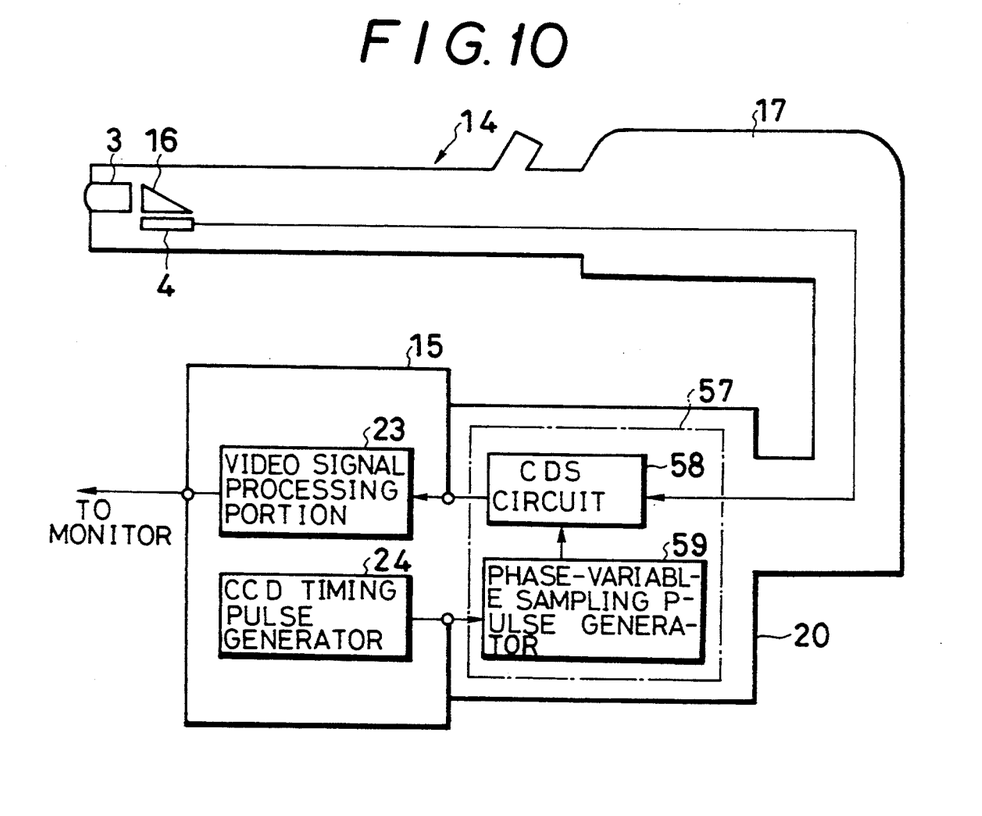
FIG. 10 shows the structure of a second embodiment of a signal processing circuit for an electronic endoscope according to the present invention.

FIG. 10 shows the structure of a second embodiment of the present invention. In this embodiment, the sample-and-hold circuit is disposed within the connecting portion 20. A setup board 57 in the connecting portion 20 shown in FIG. 10 is provided with a CDS circuit 58 and a phase-variable sampling pulse generator 59. The sample-and-hold circuit is provided in the electronic endoscope 14 in the same way as in the first embodiment, and it is possible to determine a clamping pulse and a sampling pulse having the operation timing corresponding to the length of each electronic endoscope 14.

As the CDS circuit 58, the circuit shown in FIG. 2 or the differential delay noise eliminating circuit shown in FIG. 7 is used. According to the structure of the second embodiment, it is possible to obtain a video signal whose noise is effectively eliminated by the correlated double sampling operation or the like in the same way as in the first embodiment.

Third Embodiment

A third embodiment of the present invention will be explained hereinunder with reference to FIG. 11. In this embodiment, the operating portion 17 is provided with a pulse driving circuit, a waveform shaping circuit and a power circuit together with the phase-variable sampling pulse generator. In the electronic endoscope 14 is provided a driving circuit for driving the CCD 4 which is disposed at the end portion of the electronic endoscope 14. In other words, the CCD 4 of each electronic endoscope 14 is controlled by the corresponding driving circuit.

Figure 11:
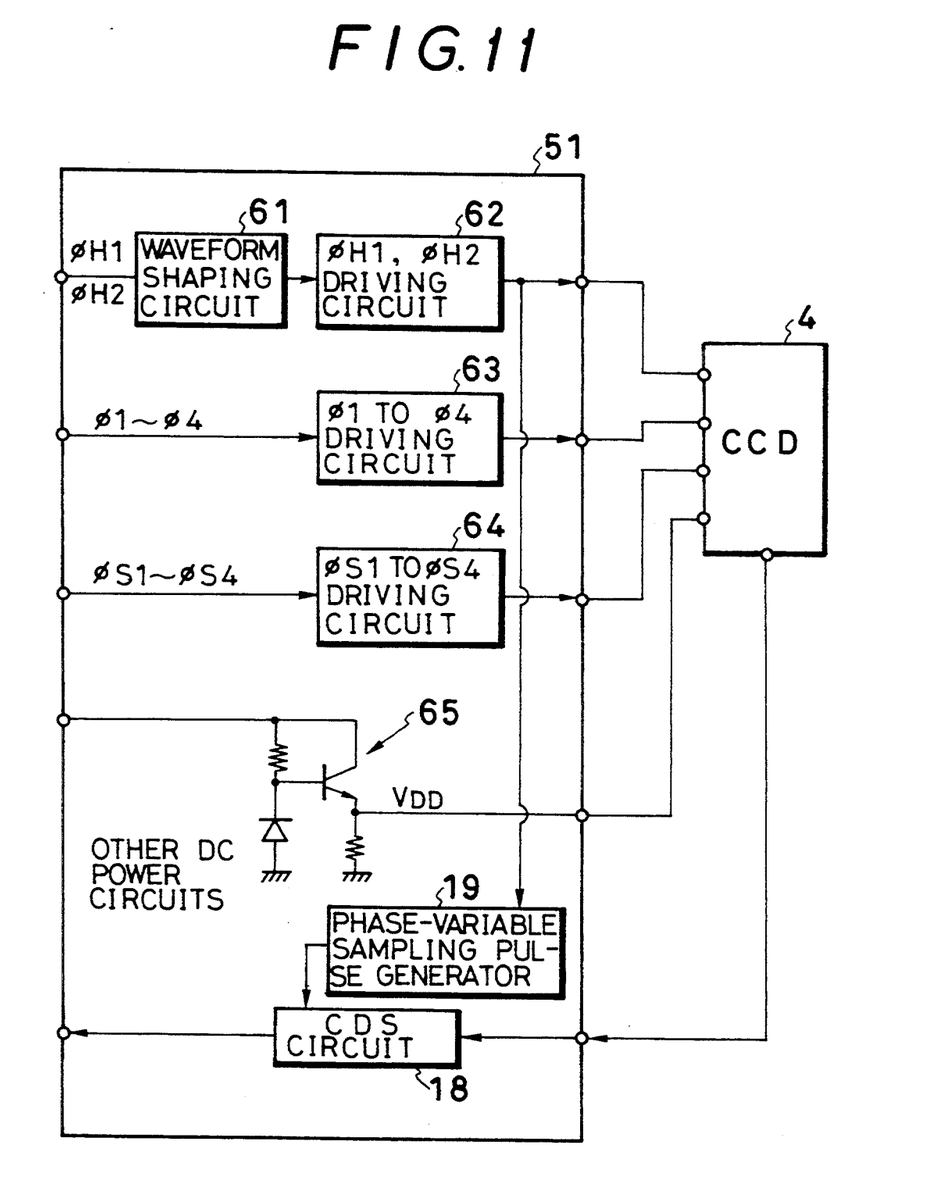
FIG. 11 is a circuit block diagram of a third embodiment of a signal processing circuit for an electronic endoscope according to the present invention.

In FIG. 11, the circuit board 51 (FIG. 9) which is attached to the operating portion 17 is provided with the CDS circuit 18, the sampling pulse generator 19, a waveform shaping circuit 61, a $\phi$H1, $\phi$H2 driving circuit 62 for driving horizontal shift resistor clocks $\phi$H1 and $\phi$H2, a $\phi$1 to $\phi$4 driving circuit 63 for driving shutter portion clocks $\phi$1 to $\phi$4, and a $\phi$S1 to $\phi$S4 driving circuit 64 for driving storage portion driving clocks $\phi$S1 to $\phi$S4. The circuit board 51 is further provided with a power source VDD circuit 65 for forming and outputting a power source VDD, and other DC power circuits. These driving circuits 62, 63, 64 and power circuits are connected to the CCD 4.

According to the structure of the third embodiment, the horizontal shift resistor clocks $\phi$H1, $\phi$H2, the shutter portion clocks $\phi$1 to $\phi$4, and the storage portion driving clocks $\phi$S1 to $\phi$S4 are supplied to the driving circuits 62, 63 and 64, respectively, and the CCD 4 is driven by the driving circuits 62, 63, and 64. The horizontal shift resistor clock $\phi$H1 is output to the phase-variable sampling pulse generator 19, and on the basis of the clock, a sampling pulse is formed.

Some conventional electronic endoscopes are provided with such driving circuits and power circuits at the end portion thereof. In this case, however, the diameter of the end portion becomes large due to the installation of the driving circuit or the like, and the performance of a solid-state image sensor is deteriorated by the influence of the heat generated by the driving circuit or the like. In contrast, since the driving circuits and the power sources are provided in the operating portion 17 in the third embodiment, it is possible to solve the above-described problems and provide a reliable electronic endoscope. In addition, the circuit board 51 is easily exposed by removing the cap 55, as shown in FIG. 9, so that it is easy to check the driving circuit or the like, exchange the circuit board 51, and so on.

In the third embodiment, the driving circuits and the power circuits of the CCD 4 are provided in the operating portion 17 together with the sample-and-hold circuit. Alternatively, these circuits may be provided on the setup board in the connecting portion together with the sample-and-hold circuit.

Fourth Embodiment

Figure 12:
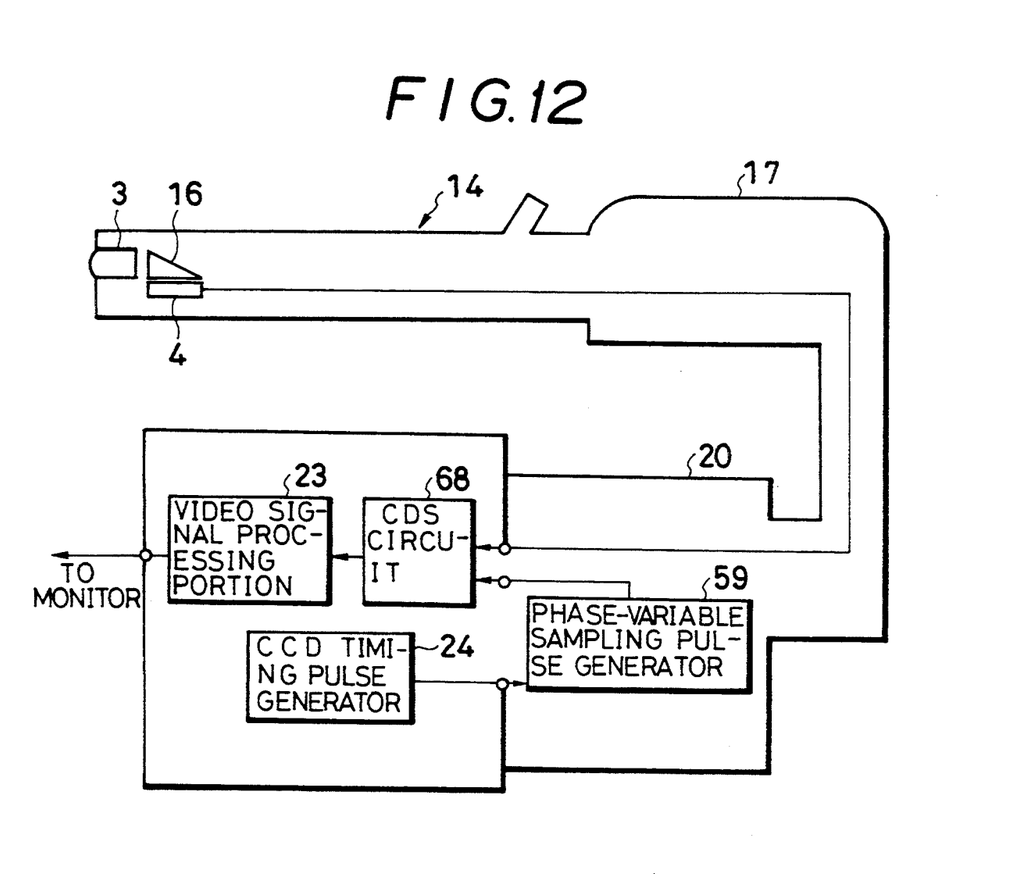
FIG. 12 shows the structure of a fourth embodiment of a signal processing circuit for an electronic endoscope according to the present invention.

FIG. 12 shows the structure of a fourth embodiment of the present invention. In this embodiment, a CDS circuit which is a part of a sample-and-hold circuit is provided in a processor apparatus. A CDS circuit 68 similar to the CDS circuit shown in FIG. 10 is provided in the processor apparatus 15, and the phase-variable sampling pulse generator 59 is provided in the connecting portion 20. This arrangement also enables the sampling operation of a video signal which is correspondent with the length of each electronic endoscope 14 by the phase-variable sampling generator 59.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A signal processing circuit for an electronic endoscope, the electronic endoscope having an operating portion, a connecting portion and a solid-state image sensor, said signal processing circuit comprising:
   a sampling pulse generator for generating a sampling pulse of a video signal, the sampling pulse generator being disposed within the electronic endoscope except at an end portion of the electronic endoscope which has the solid-state image sensor;
   a phase varying means which is incorporated into said sampling pulse generator for varying the phase of said sampling pulse so that said sampling pulse has a timing corresponding to a length of said electronic endoscope; and
   a sample-and-hold circuit for sampling and holding said video signal output from said solid-state image sensor by using said sampling pulse whose phase is adjusted by said phase varying means, wherein said sampling pulse generator incorporating said phase varying means is disposed in either of the operating portion and the connecting portion of said electronic endoscope.

2. A signal processing circuit for an electronic endoscope according to claim 1, wherein said sample-and-hold circuit having said phase varying means and said sampling pulse generator are disposed in either of the operating portion and the connecting portion of said electronic endoscope.

3. A signal processing circuit for an electronic endoscope according to claim 1, wherein a differential delay noise eliminating circuit is provided as said sample-and-hold circuit.

4. A signal processing circuit for an electronic endoscope according to claim 1, further comprising:
   a housing portion having a removable cap which is disposed at an end portion of said operating portion of said electronic endoscope, and which accommodates a circuit board provided with at least said sampling pulse generator having said phase varying means.

5. A signal processing circuit for an electronic endoscope according to claim 1, wherein a correlated double sampling circuit utilizing a clamping pulse and a sampling pulse which are correlated with each other is provided as said sample-and-hold circuit, and said sampling pulse generator adjusts the phases of said clamping pulse and said sampling pulse by said phase varying means.

6. A signal processing circuit for an electronic endoscope according to claim 4, wherein either of said correlated double sampling circuit and said differential delay noise eliminating circuit is disposed in a processor apparatus.

7. A signal processing circuit for an electronic endoscope, the electronic endoscope having an operating portion, a connecting portion and a solid state image sensor, the signal processing circuit comprising:

a phase varying circuit including a variable resistor and a capacitor for forming a pulse having timing corresponding to a length of the electronic endoscope;

a sampling pulse generator, which incorporates said phase varying circuit, which is disposed in either of the operating portion and the connecting portion of said electronic endoscope, and which forms a clamping pulse on the basis of the output of said phase varying circuit and forms a sampling pulse whose phase is shifted from said clamping pulse by a predetermined amount by a resistor and a capacitor provided at a next stage to said phase varying circuit; and a correlated double sampling circuit for sampling a video signal output from the solid-state image sensor of said electronic endoscope by using said clamping pulse and said sampling pulse which are correlated with each other and which are produced by said sampling pulse generator.

8. A signal processing circuit for an electronic endoscope, wherein a driving circuit for driving said solid-state image sensor is disposed in either of an operating portion and a connecting portion of said electronic endoscope together with said sampling pulse generator incorporating said phase varying means.

* * * * *